United States Patent
Stauss et al.

(10) Patent No.: US 8,889,141 B2
(45) Date of Patent: Nov. 18, 2014

(54) T-CELL RECEPTOR

(75) Inventors: Hans Stauss, London (GB); Shao-An Xue, London (GB); Max Topp, Wuerzburg (DE)

(73) Assignee: UCL Business PLC, London (GB)

( * ) Notice: Subject to any disclaimer, the term of this patent is extended or adjusted under 35 U.S.C. 154(b) by 101 days.

(21) Appl. No.: 13/498,561

(22) PCT Filed: Sep. 28, 2010

(86) PCT No.: PCT/GB2010/001821
§ 371 (c)(1), (2), (4) Date: Jun. 11, 2012

(87) PCT Pub. No.: WO2011/039508
PCT Pub. Date: Apr. 7, 2011

(65) Prior Publication Data
US 2012/0244132 A1   Sep. 27, 2012

(30) Foreign Application Priority Data

Sep. 29, 2009 (GB) .................................. 0917090.3

(51) Int. Cl.
*A61K 39/00* (2006.01)
*C07K 14/725* (2006.01)

(52) U.S. Cl.
CPC .................................. *C07K 14/7051* (2013.01)
USPC .................................................... 424/185.1

(58) Field of Classification Search
None
See application file for complete search history.

(56) References Cited

PUBLICATIONS

Stauss et al. (Molecular Therapy (2007) 15 10, 1744-1750).*
Murray et al. (Blood, vol. 92, No. 7 (Oct. 1), 1998: pp. 2477-2483).*
Janeway et al., Immunobiology, 5th Ed., Garland Science, pp. 106-108, 117-118 and 260-263, (2001).*
Manning et al., Immunity, vol. 8, 413-425, Apr. 1998.*
Garcia et al., Cell, vol. 122, 333-336, Aug. 12, 2005.*
Goyarts et al. (Mol Immunol. Jul. 1998;35(10):593-607).*
Stauss et al. (Molecular Therapy, vol. 15 No. 10, pp. 1744-1750, Oct. 2007).*
Diekmann et al. (J Immunol 2009; 183:1587-1597; Prepublished online Jul. 8, 2009).*
Murry et al. (Blood, vol. 92, No. 7 Oct. 1, 1998: pp. 2477-2483).*
Morgan et al. (Science. Oct. 6, 2006; 314(5796): 126-129).*
Zhao et al. (J Immunother 2006;29:398-406).*
Santomasso et al. (Proc Natl Acad Sci U S A. Nov. 27, 2007;104(48):19073-8 and supplemental pp. 1-12).*
Altschul et al., Basic local alignment search tool. *J. Mol. Biol.*, 215(3):403-10 (1990).
Ausubel (Ed) et al., Short Protocols in Molecular Biology, 4th Edition, Chapter 18—Unit 18.1, pp. 18.1-18.23 (1999).
Ausubel (Ed) et al., Short Protocols in Molecular Biology, 4th Edition, Chapter 7—Unit 7.7, pp. 7.58-7.60 (1999).
Celis et al., Identification of potential CTL epitopes of tumor-associated antigen MAGE-1 for five common HLA-A alleles. *Mol. Immunol.*, 31(18):1423-30 (1994).
Coffin (Ed.) et al., Retroviruses, pp. 758-763 (1997).
Devereux et al., A comprehensive set of sequence analysis programs for the VAX. *Nucleic Acids Res.*, 12(1 Pt 1):387-95 (1984).
Hart et al., Retroviral transfer of a dominant TCR prevents surface expression of a large proportion of the endogenous TCR repertoire in human T cells. *Gene Ther.*, 15(8):625-31 (2008).
Hildigner et al., Design of 5' untranslated sequences in retroviral vectors developed for medical use. *J. Virol.*, 73(5):4083-9 (1999).
Lewis et al., Human immunodeficiency virus infection of cells arrested in the cell cycle. *EMBO J.*, 11(8):3053-8 (1992).
Orentas et al., Retroviral transduction of a T cell receptor specific for an Epstein-Barr virus-encoded peptide. *Clin. Immunol.*, 98(2):220-8 (2001).
Tatusova et al., BLAST 2 Sequences, a new tool for comparing protein and nucleotide sequences. *FEMS Microbiol Lett.*, 174(2):247-50 (1999).
Tatusova et al., Erratum to "BLAST 2 sequences, a new tool for comparing protein and nucleotide sequences". *FEMS Microbiol. Lett.*, 177: 187-8 (1999).
International Search Report and Written Opinion from Application No. PCT/GB2010/001821, dated Apr. 20, 2011.
International Preliminary Report on Patentability, PCT/GB2010/001820, International Bureau of WIPO, completed Apr. 3, 2012.
Lee et al., HLA A2.1-restricted cytotoxic T cells recognizing a range of Epstein-Barr virus isolates through a defined epitope in latent membrane protein LMP2, *J. Virol.*, 67(12):7428-35 (1993).

* cited by examiner

*Primary Examiner* — Zachary Skelding
(74) *Attorney, Agent, or Firm* — Marshall, Gerstein & Borun LLP

(57) ABSTRACT

The present invention provides a T-cell receptor (TCR) which binds to a peptide from latent membrane protein 2 (LMP-2) from the Epstein Barr Virus (EBV) having the amino acid sequence CLGGLLTMV (SEQ ID No. 1) when presented by a major histocampatability complex (MHC) molecule. The present invention also provides a nucleotide sequence encoding such a TCR, a vector comprising such a nucleotide sequence and its use to produce a EBV-specific T-cell. The present invention also provides the use of EBV-specific T-cell for cellular immunotherapy.

6 Claims, 4 Drawing Sheets

T-CELL RECEPTOR

FIELD OF THE INVENTION

The present invention relates to a T-cell receptor (TCR) capable of recognising an antigen from Epstein Barr Virus (EBV). The present invention also relates to the use of TCR gene transfer to produce EBV-specific T cells and their use to treat and/or prevent an EBV-associated disease.

BACKGROUND TO THE INVENTION

The Epstein-Barr virus (EBV), a member of the herpesvirus family, is found throughout the world. Studies show that up to 95% of all adults have antibodies against this common virus, meaning that they have been infected at some point in their lives. EBV generally persists throughout life in most people who are infected and rarely causes any problems. In some cases, however, EBV has been linked to the development of cancers and serious conditions, including Burkitt's lymphoma, Hodgkin lymphoma, nasopharyngeal carcinoma, and post transplant lymphoproliferative disorder, a type of B-cell lymphoma which can occur in patients following solid organ or hematopoietic stem cell transplantation (HSCT).

There is thus a need for methods to treat and/or prevent EBV-associated diseases.

SUMMARY OF ASPECTS OF THE INVENTION

Figure 1:
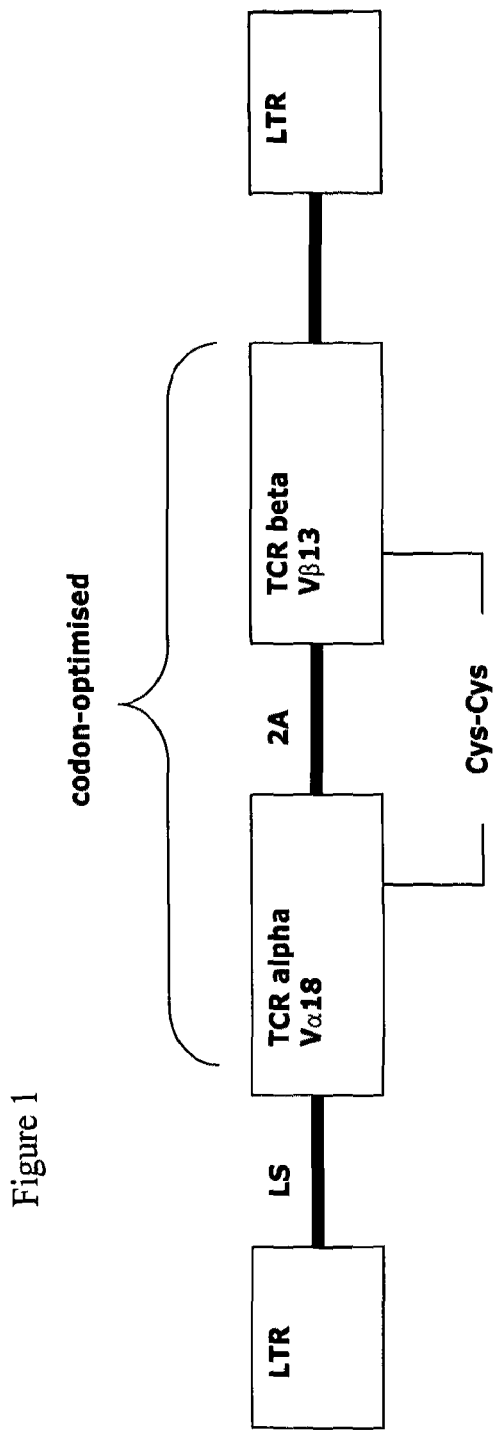
FIG. 1—Schematic of retroviral vector construct pMP71-pp65(alpha-2A-beta)-Cys1.

The present inventors have developed a cellular therapy to treat and/or prevent EBV-associated diseases which involves using TCR gene therapy to produce EBV-specific T cells.

The present inventors have assembled a T-cell receptor that is specific for the LMP-2 protein of EBV. They have also constructed a retroviral vector comprising the TCR α and β genes and used this to transduce human T cells. The cells were shown to express LMP2-specific TCR and show functional antigen specific activity.

Thus, in a first aspect, the present invention provides a T-cell receptor (TCR) specific for the LMP2 protein of Epstein Barr Virus.

The TCR may recognise the epitope CLGGLLTMV (SEQ ID No. 1) from LMP-2.

The TCR may be capable of binding to a peptide having the amino acid sequence CLGGLLTMV (SEQ ID No. 1) when presented by a major histocompatability complex (MHC) molecule.

The α chain and the β chain of the TCR each have three complementarity determining regions (CDRs). The α chain and the β chain of the TCR may have the following CDR3 sequences:

CDR3α-FCAMREGSGSARQLTFGSGTQLTVLPD (SEQ ID No. 2)

CDR3β-ASSLGPAGIQETQYFGPGTRLLVL (SEQ ID No. 3)

or a variant of those sequences having up to three amino acid changes.

The CDRs of the α chain may having the following amino acid sequences:

CDR1α-TSDQSYG (SEQ ID No. 4)

CDR2α-QGSYDEQ (SEQ ID No. 5)

CDR3α-FCAMREGSGSARQLTFGSGTQLTVLPD (SEQ ID No. 2)

or variants of those sequences having up to three amino acid changes.

The CDRs of the β chain may having the following amino acid sequences:

CDR1β-SSHAT (SEQ ID No. 6)

CDR2β-FNYEAQ (SEQ ID No. 7)

CDR3β-ASSLGPAGIQETQYFGPGTRLLVL. (SEQ ID No. 3)

or variants of those sequences having up to three amino acid changes.

The TCR of the first aspect of the invention may comprise the amino acid sequence shown as SEQ ID No. 8 or a variant thereof having at least 80% amino acid sequence identity.

The TCR of the first aspect of the invention may comprise one or more mutations at the TCR α chain/β chain interface, such that when the TCR α chain and β chain as defined in any preceding claim are expressed in a T-cell, the frequency of mis-pairing between these chains and the endogenous TCR α chain and β chain is reduced.

For example, in the TCR of the first aspect of the invention, the constant region domains of the α chain and β chain may each comprise an additional cysteine residue, enabling the formation of an extra disulphide bond between the α chain and the β chain.

The second aspect provides nucleotide sequences encoding all or a part of the TCR according to the first aspect of the invention.

A first embodiment of the second aspect of the invention relates to a nucleotide sequence encoding the α chain of a TCR according to the first aspect of the invention.

The nucleotide sequence of this first embodiment may comprise bases 1-810 of the nucleotide sequence shown as SEQ ID No. 9 or a variant thereof having at least 80% sequence identity.

A second embodiment of the second aspect of the invention relates to a nucleotide sequence encoding the β chain of a TCR according to the first aspect of the invention.

The nucleotide sequence of this second embodiment may comprise bases 886-1812 of SEQ ID No. 9 or a variant thereof having at least 80% sequence identity.

A third embodiment of the second aspect of the invention relates to a nucleotide to sequence encoding a TCR α chain linked to a TCR β chain.

The nucleotide sequence may comprise the TCR α and β genes linked by an internal self-cleaving sequence.

The nucleotide sequence of this third embodiment may comprise the sequence shown as SEQ ID No. 9 or a variant thereof having at least 80% sequence identity.

In a third aspect, the present invention provides a vector comprising a nucleotide sequence according to the second aspect of the invention. The vector may, for example, be a retroviral vector.

In a fourth aspect, the invention provides a cell which comprises a nucleotide sequence according to the second aspect of the invention. The cell may, for example be a T-cell or a stem cell. The cell may be derived from a T-cell isolated from a subject.

In a fifth aspect the present invention provides a method for producing a cell according to the fourth aspect of the invention which comprises the step of transducing or transfecting a cell in vitro or ex vivo with a vector according to the third aspect of the invention.

In a sixth aspect, the present invention provides a method for treating and/or preventing a disease associated with EBV in a subject which comprises the step of adoptive transfer of a EBV-specific T-cell to the subject, wherein the EBV-specific T-cell is made by TCR gene transfer.

The T-cell comprises one or more heterologous nucleotide sequence(s) capable of encoding a EBV-specific TCR.

The TCR may be in accordance with the first aspect of the invention.

The method may be used to treat or prevent an EBV-associated disease such as EBV positive Hodgkin Lymphoma, EBV positive Nasopharyngeal Carcinoma or EBV positive post transplant lymphoproliferative disorder (PTLD).

The present invention also provides a vector according to the third aspect of the invention or a cell according to the fourth aspect of the invention for use in treating and/or preventing a disease associated with EBV in a subject.

The present invention also provides a pharmaceutical composition comprising a vector according to the third aspect of the invention or a cell according to the fourth aspect of the invention.

The present invention also provides the use of a TCR according to the first aspect of the invention, a nucleotide sequence according to the second aspect of the invention, a vector according to the third aspect of the invention, or a cell according to the fourth aspect of the invention in the manufacture of a medicament for use in treating and/or preventing a disease associated with EBV in a subject.

DETAILED DESCRIPTION

T-Cell Receptor

During antigen processing, antigens are degraded inside cells and then carried to the cell surface by major histocompatability complex (MHC) molecules. T cells are able to recognise this peptide: complex at the surface of the antigen presenting cell. There are two different classes of MHC molecules: MHC I and MHC II, that deliver peptides from different cellular compartments to the cell surface.

The T cell receptor or TCR is the molecule found on the surface of T cells that is responsible for recognizing antigens bound to MHC molecules. The TCR heterodimer consists of an alpha and beta chain in 95% of T cells, whereas 5% of T cells have TCRs consisting of gamma and delta chains.

Engagement of the TCR with antigen and MHC results in activation of its T lymphocyte through a series of biochemical events mediated by associated enzymes, co-receptors, and specialized accessory molecules.

Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end.

The variable domain of both the TCR α-chain and β-chain have three hypervariable or complementarity determining regions (CDRs). CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule.

The constant domain of the TCR domain consists of short connecting sequences in which a cysteine residue forms a disulfide bond, making a link between the two chains. The TCR of the present invention may have an additional cysteine residue in each of the α and β chains such that the TCR comprises two disulphide bonds in the constant domains (see below).

The structure allows the TCR to associate with other molecules like CD3 which possess three distinct chains (γ, δ, and ε) in mammals and the ζ-chain. These accessory molecules have negatively charged transmembrane regions and are vital to propagating the signal from the TCR into the cell. The CD3- and ζ-chains, together with the TCR, form what is known as the T cell receptor complex.

The signal from the T cell complex is enhanced by simultaneous binding of the MHC molecules by a specific co-receptor. On helper T cells, this co-receptor is CD4 (specific for class II MHC); whereas on cytotoxic T cells, this co-receptor is CD8 (specific for class I MHC). The co-receptor not only ensures the specificity of the TCR for an antigen, but also allows prolonged engagement between the antigen presenting cell and the T cell and recruits essential molecules (e.g., LCK) inside the cell involved in the signaling of the activated T lymphocyte.

The term "T-cell receptor" is thus used in the conventional sense to mean a molecule capable of recognising a peptide when presented by an MHC molecule. The molecule may be a heterodimer of two chains α and β (or optionally γ and δ) or it may be a single chain TCR constuct.

The present invention also provides the α chain or β chain from such a T cell receptor.

The TCR of the present invention may be a hybrid TCR comprising sequences derived from more than one species. For example, it has surprisingly been found that murine TCRs have been found to be more efficiently expressed in human T cells than human TCRs. The TCR may therefore comprise human variable regions and murine constant regions. A disadvantage of this approach is that the murine constant sequences may trigger an immune response, leading to rejection of the transferred T cells. However, the conditioning regimens used to prepare patients for adoptive T-cell therapy may result in sufficient immunosuppression to allow the engraftment of T cells expressing murine sequences.

CDR Sequences

The TCR of the first aspect of the invention comprises two chains (α and β) each of which comprise three complementarity determining regions.

T-cell receptor diversity is focused on CDR3 and this region is primarily responsible for antigen recognition. The sequences of the CDR3 regions from the TCR of the present invention may be:

(SEQ ID No. 2)
CDR3α-FCAMREGSGSARQLTFGSGTQLTVLPD (SEQ ID No. 3)
CDR3β-ASSLGPAGIQETQYFGPGTRLLVL or as variant of those sequences having up to three amino acid changes.

The α chain may comprise CDRs having the following amino acid sequences:

```
                                    (SEQ ID No. 4)
    CDR1α-TSDQSYG (SEQ ID No. 5)
    CDR2α-QGSYDEQ (SEQ ID No. 2)
    CDR3α-FCAMREGSGSARQLTFGSGTQLTVLPD.
```

The β chain may comprise CDRs having the following amino acid sequences:

```
                                    (SEQ ID No. 6)
    CDR1β-SSHAT (SEQ ID No. 7)
    CDR2β-FNYEAQ (SEQ ID No. 3)
    CDR3β-ASSLGPAGIQETQYFGPGTRLLVL.
```

The CDRs may comprise one or more "changes", such as substitutions, additions or deletions from the given sequence, provided that the TCR retains the capacity to bind the pp65 epitope:MHC complex. The change may involve substitution of an amino acid for a similar amino acid (a conservative substitution). A similar amino acid is one which has a side chain moiety with related properties as grouped together, for example as shown below:
(i) basic side chains: lysine, arginine, histidine
(ii) acidic side chains: aspartic acid and glutamic acid
(iii) uncharged polar side chains: asparagine, glutamine, serine, threonine and tyrosine
(iv) non-polar side chains: glycine, alanine, valine, leucine, isoleucine, proline, phenylalanine, methionine, tryptophan and cysteine.

Any amino acid changes should maintain or improve the capacity to bind MHC molecules. For example, if the peptide is capable of binding MHC molecules of the HLA-A*0201 allele then it is preferred that the amino acids at position 2 of the peptide (i.e. the second amino acid from the N-terminus) are leucine or methionine, although isoleucine, valine, alanine and threonine are also tolerated. It is also preferred that the amino acid at position 9 or 10 is valine, leucine or isoleucine, although alanine, methionine and threonine are also tolerated. The preferred MHC binding motifs or other HLA alleles are disclosed in Celis et al, Molecular Immunology, Vol. 31, 8, Dec. 1994, pages 1423 to 1430.

The TCR of the first aspect of the invention may comprise the following amino acid sequence (SEQ ID No. 8) or a variant thereof having at least 70%, 80%, 90%, or 95% amino acid sequence identity:

```
EBVa14-p2A-Vb7.7-aa:
MSLSSLLKVV TASLWLGPGI AQKITQTQPG MFVQEKEAVT

LDCTYDTSDQ SYGLFWYKQP SSGEMIFLIY QGSYDEQNAT

EGRYSLNFQK ARKSANLVIS ASQLGDSAMY FCAMREGSGS

ARQLTFGSGT QLTVLPDIQN PEPAVYQLKD PRSQDSTLCL

FTDFDSQINV PKTMESGTFI TDKCVLDMKA MDSKSNGAIA

WSNQTSFTCQ DIFKETNATY PSSDVPCDAT LTEKSFETDM
```
```
                    -continued
NLNFQNLSVM GLRILLLKVA GFNLLMTLRL WSSGSGATNF

SLLKQAGDVE ENPGPMGTSL LCWVVLGFLG TDHTGAGVSQ

SPRYKVTKRG QDVTLRCDPI SSHATLYWYQ QALGQGPEFL

TYFNYEAQPD KSGLPSDRFS AERPEGSIST LTIQRTEQRD

SAMYRCASSL GPAGIQETQY FGPGTRLLVL EDLRNVTPPK

VSLFEPSKAE IANKQKATLV CLARGFFPDH VELSWWVNGK

EVHSGVCTDP QAYKESNYSY CLSSRLRVSA TFWHNPRNHF

RCQVQFHGLS EEDKWPEGSP KPVTQNISAE AWGRADCGIT

SASYHQGVLS ATILYEILLG KATLYAVLVS GLVLMAMVKK

KNS*

Blue: Constant sequences.
Red: cysteine molecules for the interchain
disulphide bound.
Pink: 2A sequences.
Black: Variable sequences
Underlined CDR1, 2 and 3 regions.
```

Variant sequences may comprise amino acid additions, deletions and/or insertions. The variation may be concentrated in one or more regions, such as the constant regions, the linker, or the framework regions of the α or β chains, or they may be spread throughout the molecule.

Identity comparisons can be conducted by eye, or more usually, with the aid of readily available sequence comparison programs. These commercially available computer programs can calculate % identity between two or more sequences.

% identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % identity therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. BLAST 2 Sequences is also available for comparing protein and nucleotide sequences (see FEMS Microbiol Lett 1999 174(2): 247-50; FEMS Microbiol Lett 1999 177(1): 187-8 and tatiana@ncbi.nlm.nih.gov).

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P<br>I L V |
| | Polar-uncharged | C S T M<br>N Q |
| | Polar-charged | D E<br>K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

LMP-2

The first aspect of the invention relates to a TCR which binds specifically to EBV latent membrane protein 2 (LMP-2). LMP-2 refers to two viral proteins associated with Epstein-Barr virus, LMP-2A and LMP-2B.

LMP-2A/LMP-2B are transmembrane proteins that act to block tyrosine kinase signaling. It is believed that they act to inhibit activation of the viral lytic cycle.

LMP-2A has the sequence given below:

```
  1 mgslemvpmg agppspggdp dgddggnnsq ypsasgssgn tptppndeer esneeppppy
 61 edpywgngdr hsdyqplgtq dqslylglqh dgndglpppp ysprddssqh iyeeagrgsm
121 npvclpviva pylfwlaaia ascftasvst vvtatglals llllaavass yaaaqrkllt
181 pvtvltavvt ffaicltwri edppfnsllf allaaagglq giyvlvmlvl lilayrrrwr
241 rltvcggimf lacvlvlivd avlqlspllg avtvvsmtll llafvlwlss pgglgtlgaa
301 lltlaaalal laslilgtln lttmfllmll wtlvvllics scsscplski llarlflyal
361 allllasali aggsilqtnf kslsstefip nlfcmllliv agilfilail tewgsgnrty
421 gpvfmclggl ltmvagavwl tvmtntllsa wiltagflif ligfalfgvi rccryccyyc
481 ltleseerpp tpyrntv
```

LMP-2B has the sequence given below:

```
  1 mnpvclpviv apylfwlaai aascftasvs tvvtatglal sllllaavas syaaagrkll
 61 tpvtvltavv tffaicltwr iedppfnsll fallaaaggl qgiyvlvmlv llilayrrrw
121 rrltvcggim flacvlvliv davlqlspll gavtvvsmtl lllafvlwls spgglgtlga
181 alltlaaala llaslilgtl nlttmfllml lwtlvvllic sscsscplsk illarlflya
241 lallllasal iaggsilqtn fkslsstefi pnlfcmllli vagilfilai ltewgsgnrt
301 ygpvfmclgg lltmvagavw ltvmtntlls awiltagfli fligfalfgv irccryccyy
361 cltleseerp ptpyrntv
```

The peptide CLGGLLTMV recognised by the T-cell receptor of the first aspect of the invention is shown in red in each sequence.

The TCR may recognise all or part of this sequence. The TCR may recognise a part of this sequence together with one or more (for example up to 5) upstream or downstream amino acids. The TCR may recognise all or part of the following sequence GPVFMCLGGLTMVAGAVW.

Major Histocompatability Complex (MHC) Molecules

The TCR binds to the peptide as a peptide:MHC complex. The MHC molecule may be an MHC class I or II molecule. The complex may be on the surface of an antigen presenting cell, such as a dendritic cell or a B cell, or it may be immobilised by, for example, coating on to a bead or plate.

The human leukocyte antigen system (HLA) is the name of the major histocompatibility complex (MHC) in humans and includes that HLA class I antigens (A, B & C) and HLA class II antigens (DP, DQ, & DR).

Reducing Mispairing

The TCR of the first aspect of the invention may be expressed in a T cell to alter its antigen specificity. TCR-transduced T cells express at least two TCR alpha and two TCR beta chains. While the endogenous TCR alpha/beta chains form a receptor that is self-tolerant, the introduced TCR alpha/beta chains form a receptor with defined specificity for the given target antigen.

However, mis-pairing between endogenous and introduced chains may occur to form novel receptors, which might display unexpected specificities for self-antigens and cause autoimmune damage when transferred into patients.

Hence, several strategies have been explored to reduce the risk of mis-pairing between endogenous and introduced TCR chains. Mutations of the TCR alpha/beta interface is one strategy currently employed to reduce unwanted mis-pairing.

For example, the introduction of an additional cysteine in the constant domains of the alpha and beta chain allows the formation of an additional disulfide bond and enhances the pairing of the introduced chains while reducing mis-pairing with wild type chains.

The TCR of the present invention may therefore comprise an additional cysteine in the α chain and the β chain, which form an additional disulphide bond between the two chains, making two disulphide bonds in total.

The additional cysteines are shown in red in the amino acid sequence shown above in the Section "CDR sequences"

Nucleotide Sequence

The second aspect of the invention relates to a nucleotide sequence encoding a TCR receptor of the first aspect of the invention or a part thereof, such as one or more CDR; the variable sequence of the α chain or the β chain; the α chain and/or the β chain.

The nucleotide sequence may be double or single stranded, and may be RNA or DNA.

The nucleotide sequence may be codon optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation may also involve the removal of mRNA instability motifs and cryptic splice sites.

The nucleotide sequence of the second aspect of the invention may comprise all or part of the following sequence (SEQ ID No. 9) or a variant thereof having at least 70%, 80%, 90%, or 95% amino acid sequence identity:

```
EBVa14-p2A-Vb7.7-coding seq:
ATGTCACTTT CTAGCCTGCT GAAGGTGGTC ACAGCTTCAC

TGTGGCTAGG ACCTGGCATT GCCCAGAAGA TAACTCAAAC

CCAACCAGGA ATGTTCGTGC AGGAAAAGGA GGCTGTGACT

CTGGACTGCA CATATGACAC CAGTGATCAA AGTTATGGTC

TCTTCTGGTA CAAGCAGCCC AGCAGTGGGG AAATGATTTT

TCTTATTTAT CAGGGGTCTT ATGACGAGCA AAATGCAACA

GAAGGTCGCT ACTCATTGAA TTTCCAGAAG GCAAGAAAAT

CCGCCAACCT TGTCATCTCC GCTTCACAAC TGGGGACTC

AGCAATGTAT TTCTGTGCAA TGAGAGAGGG TTCTGGTTCT

GCAAGGCAAC TGACCTTTGG ATCTGGGACA CAATTGACTG

TTTTACCTGA TATCCAGAAC CCTGAGCCCG CGGTGTACCA

GCTGAAGGAC CCCAGAAGCC AGGACAGCAC CCTGTGCCTG

TTCACCGACT TCGACAGCCA GATCAACGTG CCCAAGACAA

TGGAAAGCGG CACCTTCATC ACCGACAAGT GCGTGCTGGA

CATGAAGGCT ATGGACAGCA AGAGCAACGG CGCCATCGCC

TGGTCCAACC AGACCTCCTT CACATGCCAA GACATCTTCA

AAGAGACCAA CGCCACCTAC CCCAGCAGCG ACGTGCCCTG

CGATGCCACT CTCACCGAGA AGAGCTTCGA GACCGACATG

AACCTGAACT TCCAGAACCT GAGCGTGATG GGCCTGAGAA

TCCTGCTCCT GAAAGTGGCC GGCTTCAACC TGCTGATGAC

CCTGCGGCTC TGGAGTTCTG GCAGCGGCGC TACCAACTTC

AGCCTGCTGA AGCAGGCCGG CGACGTGGAG GAAAACCCTG

GCCCCATGGG TACCAGTCTC CTATGCTGGG TGGTCCTGGG

TTTCCTAGGG ACAGATCACA CAGGTGCTGG AGTCTCCCAG

TCTCCCAGGT ACAAAGTCAC AAAGAGGGGA CAGGATGTAA

CTCTCAGGTG TGATCCAATT TCGAGTCATG CAACCCTTTA

TTGGTATCAA CAGGCCCTGG GGCAGGGCCC AGAGTTTCTG

ACTTACTTCA ATTATGAAGC TCAACCAGAC AAATCAGGGC

TGCCCAGTGA TCGGTTCTCT GCAGAGAGGC CTGAGGGATC

CATCTCCACT CTGACGATTC AGCGCACAGA GCAGCGGGAC

TCAGCCATGT ATCGCTGTGC TAGCAGCTTA GGTCCCGCAG

GGATCCAAGA GACCCAGTAC TTCGGGCCAG GCACGCGGCT

CCTGGTGCTC GAGGACCTGC GGAACGTGAC CCCCCCCAAG

GTGTCCCTGT TCGAGCCCAG CAAGGCCGAG ATCGCCAACA

AGCAGAAAGC CACACTGGTC TGTCTGGCTA GGGGCTTCTT

CCCCGACCAC GTGGAGCTGT CTTGGTGGGT CAACGGCAAA
```

```
                  -continued
GAAGTCCATA GCGGCGTCTG CACCGACCCT CAGGCTTACA

AAGAGAGCAA CTACTCCTAC TGCCTGAGCA GCCGGCTGAG

AGTGAGCGCC ACCTTCTGGC ACAACCCCCG GAACCACTTC

CGGTGCCAGG TGCAGTTCCA CGGCCTGAGC GAAGAGGACA

AGTGGCCTGA GGGCTCCCCC AAGCCCGTGA CCCAGAACAT

CAGCGCCGAG GCCTGGGGCA GAGCCGACTG CGGCATCACC

AGCGCCAGCT ACCACCAGGG CGTGCTGTCC GCCACCATCC

TGTACGAGAT CCTGCTGGGC AAGGCCACAC TGTACGCCGT

GCTGGTGTCC GGCCTGGTCC TGATGGCTAT GGTGAAGAAG

AAGAACAGCT GA
```

The nucleotide sequence may comprise the part(s) of the above sequence which encode one or more CDRs or a variant thereof having at least 70%, 80%, 90%, or 95% amino acid sequence identity, these parts are the following sections of SEQ ID No. 9:
CDR1α: 139-159
CDR2α: 211-231
CDR3α: 331-411
CDR1β: 1021-1035
CDR2β: 1087-1104
CDR3β: 1219-1290

The nucleotide sequence may comprise the part(s) of the above sequence which encode one or more variable regions or a variant thereof having at least 70%, 80%, 90%, or 95% amino acid sequence identity, these parts are:
Vα: 1-411
Vβ: 886-1290

The nucleotide sequence may comprise the part(s) of the above sequence which encode the α chain and/or the β chain or a variant thereof having at least 70%, 80%, 90%, or 95% amino acid sequence identity, these parts are:
α—1-810
β—886-1812.

The variant sequences may have additions, deletions or substitutions or one or more bases. If the variation involves addition(s) or deletion(s) they may either occur in threes or be balanced (i.e. an addition for each deletion) so that the variation does not cause a frame-shift for translation of the remainder of the sequence.

Some or all of the variations may be "silent" in the send that they do not affect the sequence of the encoded protein due to the degeneracy of the protein code.

Some or all of the variations may produce conservative amino acid substitutions as explained above. The variation may be concentrated in one or more regions, such as the regions encoding the constant regions, the linker, or the framework regions of the α or β chains, or they may be spread throughout the molecule.

The variant sequence should retain the capacity to encode all or part of a sequence which binds an CLGGLLTMV:MHC complex.

Vector

The present invention also provides a vector comprising a nucleotide sequence according to the second aspect of the invention.

The term "vector" includes an expression vector i.e. a construct capable of in vivo or in vitro/ex vivo expression.

Viral delivery systems include but are not limited to adenovirus vector, an adeno-associated viral (AAV) vector, a herpes viral vector, retroviral vector, lentiviral vector, baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses also belong to the retrovirus family, but they can infect both dividing and non-dividing cells (Lewis et al (1992) EMBO J. 3053-3058).

The vector may be capable of transferring a nucleotide according to the second aspect of the invention to a cell, such as a T-cell, such that the cell expresses a EBV-specific TCR. The vector should ideally be capable of sustained high-level expression in T cells, so that the introduced TCR may compete successfully with the endogenous TCR for a limited pool of CD3 molecules.

The vector may be a retroviral vector. The vector may be based on or derivable from the MP71 vector backbone. The vector may lack a full-length or truncated version of the Woodchuck Hepatitis Response Element (WPRE).

For efficient infection of human cells, viral particles may be packaged with amphotropic envelopes or gibbon ape leukemia virus envelopes.

Increasing the supply of CD3 molecules may increase TCR expression in gene modified cells. The vector may therefore also comprise the genes for CD3-gamma, CD3-delta, CD3-epsilon and/or CD3-zeta. The vector may just comprise the gene for CD3-zeta. The genes may be linked by self-cleaving sequences, such as the 2A self-cleaving sequence. Alternatively one or more separate vectors may be provided encoding CD3 gene for co-transfer with the TCR-encoding vector(s).

Cell

The fourth aspect of the present invention relates to a cell which comprises a nucleotide sequence according to the second aspect of the invention. The cell may express a T-cell receptor of the first aspect of the invention.

The cell may be a T-cell. The cell may be derived from a T-cell isolated from a subject. The T-cell may be part of a mixed cell population isolated from the subject, such as a population of peripheral blood lymphocytes (PBL). T cells within the PBL population may be activated by methods known in the art, such as using anti-CD3 and CD28 antibodies.

The T-cell may be a CD4+ helper T cell or a CD8+ cytotoxic T cell. The cell may be in a mixed population of CD4+ helper T cell/CD8+ cytotoxic T cells. Polyclonal activation, for example using anti-CD3 antibodies optionally in combination with anti-CD28 antibodies will trigger the proliferation of CD4+ and CD8+ T cells, but may also trigger the proliferation of CD4+25+ regulatory T-cells.

TCR gene transfer into regulatory T cells is undesirable as they may suppress the anti-viral activity of the gene-modified cytotoxic and helper T cells. The CD4+CD25+ population may therefore be depleted before TCR gene transfer.

The present invention also provides a method of producing a cell according to the fourth aspect of invention which comprises the step of transfecting or transducing a cell in vitro or ex vivo with a vector according to the third aspect of the invention.

The cell may be isolated from the subject to which the genetically modified cell is to be adoptively transferred. In this respect, the cell may be made by isolating a T-cell from a subject, optionally activating the T-cell, TCR gene transfer ex vivo and subsequent immunotherapy of the subject by adoptive transfer of the TCR-transduced cells.

Alternatively the cell may be isolated from a different subject, such that it is allogeneic. The cell may be isolated from a donor subject. For example, if the subject is undergoing allogeneic haematopoietic stem cell transplantation (Allo-HSCT), the cell may be derived from the donor, from which the HSCs are derived. If the subject is undergoing or has undergone solid organ transplant, the cell may be derived from the subject from whom the solid organ was derived.

Alternatively the cell may be, or be derived from, a stem cell, such as a haemopoietic stem cell (HSC). Gene transfer into HSCs does not lead to TCR expression at the cell surface as stem cells do not express the CD3 molecules. However, when stem cells differentiate into lymphoid precursors that migrate to the thymus, the initiation of CD3 expression leads to the surface expression of the introduced TCR in thymocytes.

An advantage of this approach is that the mature T cells, once produced, express only the introduced TCR and little or no endogenous TCR chains, because the expression of the introduced TCR chains suppresses rearrangement of endogenous TCR gene segments to form functional TCR alpha and beta genes.

A further benefit is that the gene-modified stem cells are a continuous source of mature T-cells with the desired antigen specificity. The cell may therefore be a gene-modified stem cell, which, upon differentiation, produces a T-cell expressing a TCR of the first aspect of the invention. The present invention also provides a method of producing a T-cell expressing a TCR of the first aspect of the invention by inducing the differentiation of a stem cell which comprises a nucleotide sequence according to the second aspect of the invention.

A disadvantage of the stem cell approach is that TCRs with the desired specificity may get deleted during T-cell development in the thymus or may induce tolerance when expressed in peripheral T-cells. Another possible issue is the risk of insertional mutagenesis in stem cells.

EBV-Associated Diseases

The present invention also relates to a method for treating and/or preventing a disease associated with EBV in a subject which comprises the step of adoptive transfer of a EBV-specific T-cell to the subject.

The EBV-specific T-cell may recognise the LMP-2 protein. The EBV-specific T cell may recognise the epitope CLG-GLLTMV.

The term 'preventing' is intended to refer to averting, delaying, impeding or hindering the contraction of the disease. The treatment may, for example, prevent or reduce the likelihood of EBV infection.

'Treating' as used herein refers to caring for a diseased subject, in order to ameliorate, cure or reduce the symptoms of the disease, or reduce or halt the progression of the disease. It also refers to treatment which renders the virally-infected subject non-infectious to other subjects. The treatment may reduce the EBV viral load.

EBV-specific T cells could be used to treat any EBV-associated condition, in which the LMP-2 antigen in expressed.

For example, EBV-specific T cells could be used in the management of EBV positive Hodgkin Lymphoma, EBV positive Nasopharyngeal Carcinoma or EBV positive post transplant lymphoproliferative disorder (PTLD). PTLD occurs post solid organ transplants (kidney, heart, lung, liver) and post allogeneic HSCT.

Burkitt's lymphoma is the most common childhood malignancy in equatorial Africa. Tumors are characteristically located in the jaw. Genetic studies have shown that in equatorial Africa (where over 95% of children have been infected with EBV by age 3), the vast majority of Burkitt lymphomas originate from an EBV-infected lymphocyte.

Hodgkin's lymphoma is characterized by the orderly spread of disease from one lymph node group to another, and by the development of systemic symptoms with advanced disease. EBV genetic material is found in up to 50% of cases of Hodgkin lymphoma in certain geographic areas and patient populations.

Nasopharyngeal carcinoma is one of the most common cancers in southern China. It originates in the nasopharynx, the uppermost region of the pharynx or "throat", where the nasal passages and auditory tubes join the remainder of the upper respiratory tract.

Post-transplant lymphoproliferative disease (PTLD) refers to a category of conditions that may develop in people following an organ transplant. The EBV virus has been implicated in the majority of cases of PTLD. Manifestations can vary, ranging from an increased number of lymphocytes in the bloodstream to blood-cell malignancies such as B-cell lymphoma.

PTLD is an uncontrolled proliferation of B cell lymphocytes following infection with Epstein-Barr virus.

Depletion of T cells by use of anti-T cell antibodies in the prevention or treatment of transplant rejection further increases the risk of developing post-transplant lymphoproliferative disorder.

Polyclonal PTLD may form tumor masses and present with symptoms due to a mass effect, e.g. symptoms of bowel obstruction. Monoclonal forms of PTLD tend to form a disseminated malignant lymphoma.

PTLD may spontaneously regress on reduction or cessation of immunosuppressant medication, and can also be treated with addition of anti-viral therapy.

Hematopoietic stem cell transplantation (HSCT) is the transplantation of blood stem cells derived from the bone marrow or blood. Stem cell transplantation is most often performed for people with diseases of the blood, bone marrow, or certain types of cancer.

With the availability of the stem cell growth factors GM-CSF and G-CSF, most hematopoietic stem cell transplantation procedures are now performed using stem cells collected from the peripheral blood, rather than from the bone marrow. Collecting peripheral blood stem cells provides a bigger graft, does not require that the donor be subjected to general anesthesia to collect the graft, results in a shorter time to engraftment, and may provide for a lower long-term relapse rate.

Hematopoietic stem cell transplantation remains a risky procedure with many possible complications; it has traditionally been reserved for patients with life-threatening diseases. While occasionally used experimentally in nonmalignant and nonhematologic indications such as severe disabling autoimmune disease and cardiovascular disease, the risk of fatal complications appears too high to gain wider acceptance.

Many recipients of HSCTs are multiple myeloma or leukemia patients who would not benefit from prolonged treatment with, or are already resistant to, chemotherapy. Candidates for HSCTs include pediatric cases where the patient has an inborn defect such as severe combined immunodeficiency or congenital neutropenia with defective stem cells, and also children or adults with aplastic anemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumor and Hodgkin's disease. More recently non-myeloablative, or so-called "mini transplant," procedures have been developed that require smaller doses of preparative chemo and radiation. This has allowed HSCT to be conducted in the elderly and other patients who would otherwise be considered too weak to withstand a conventional treatment regimen.

In addition highly immunosuppressive (or T cell depleted) reduced intensity conditioning Allo-HSCTs have been developed. These approaches reduce the toxicity of transplantation in older patients with more co-morbidities.

Allogeneic HSCT involves two people: the (healthy) donor and the (patient) recipient. Allogeneic HSC donors must have a tissue (HLA) type that matches the recipient. Matching is performed on the basis of variability at three or more loci of the (HLA) gene, and a perfect match at these loci is preferred. Even if there is a good match at these critical alleles, the recipient will require immunosuppressive medications to mitigate graft-versus-host disease. Allogeneic transplant donors may be related (usually a closely HLA matched sibling), syngeneic (a monozygotic or 'identical' twin of the patient—necessarily extremely rare since few patients have an identical twin, but offering a source of perfectly HLA matched stem cells) or unrelated (donor who is not related and found to have very close degree of HLA matching). About 25 to 30% of allogeneic HSCT recipients have an HLA-identical sibling. Allogeneic transplants are also performed using umbilical cord blood as the source of stem cells. In general, by transplanting healthy stem cells to the recipient's immune system, allogeneic HCSTs appear to improve chances for cure or long-term remission once the immediate transplant-related complications are resolved.

The subject may be a human subject. In particular the subject may be a transplant recipient.

The invention will now be further described by way of Examples, which are meant to serve to assist one of ordinary skill in the art in carrying out the invention and are not intended in any way to limit the scope of the invention.

EXAMPLES

Example 1

Construction of a Retroviral Vector to Deliver EBV-Specific TCR Genes

An important issue for TCR gene therapy is the selection of vectors capable of sustained high-level expression in T lymphocytes. High expression levels are required to allow the introduced TCR to compete with the endogenous TCR for a limited pool of CD3 molecules. Further requirements for TCR gene therapy are (i) a transduction efficiency of up to 30% with minimal ex vivo manipulation, (ii) the absence of replication competent vectors, and (iii) stable TCR expression over time to allow for memory development.

In this study the MP71 vector backbone was used with a codon-optimised TCR sequence and an additional cysteine in each alpha and beta chain constant region to enhance gene expression and minimize mis-pairing with endogenous TCR chains. The MP71 vector backbone has been described previously (Hildigner et al (1999) J. Virol. 73:4083-4089). The LTR of the MP71 vector is derived from the Myeloproliferative Sarcroma Virus (MPSV) and the leader sequence (LS) is derived from the Mouse Embryonic Stem Cell Virus (MESV). The leader sequence was designed to increase vector safety in clinical applications. All ATG codons have been removed to decrease the risk of possible protein/peptide production and reduce the likelihood of homologous recombination with endogenous retroviral sequences. The expression of genes inserted into MP71 is enhanced by a minimal splice acceptor site at the 3' end of the leader sequence. The original MP71 vector contained a full length Woodchuck Hepatitis Response Element (WPRE) to enhance gene expression at the post-transcriptional level. The MP71 vector containing a truncated WPRE with mutated ATG codons is currently used in Germany in a clinical trial using gene-modified T cells in HIV patients.

The present inventors have further modified the MP71 vector and tested variants without any WPRE sequences. The vector comprises the EBV TCR alpha and beta genes, linked via an internal self-cleaving porcine teschovirus 2A sequence, as shown in FIG. 1. The alpha and beta TCR genes were synthesised based on dominant TCR usage by EBV LMP-2-specific CTL clones. The amino acid sequence for the TCR alpha-2A-TCR beta product is given as SEQ ID No. 8 and its coding sequence given as SEQ ID No. 9.

Example 2

Production of EBV LMP-2-Specific TCR-Transduced Human T Cells

Human T cell receptor (TCR) genes specific for EBV were transduced into human T cells by using retroviral vectors carrying the desired TCR genes. Briefly, amphotropic packaging cells expressing the retroviral gag-pol genes were transfected with the specified TCR-retroviral vectors by using calcium phosphate precipitation method. After the retroviral transfection, the transfection medium was changed into human T cell medium for the harvesting of retroviral supernatant. The collected retroviral supernatant containing the viral particles expressing the desired TCR genes were then used to infect/transduce activated human T cells. 24 hours later, the introduced TCR genes are expressed on the surface of transduced T cells, and can be detected by FACS staining.

Figure 2:
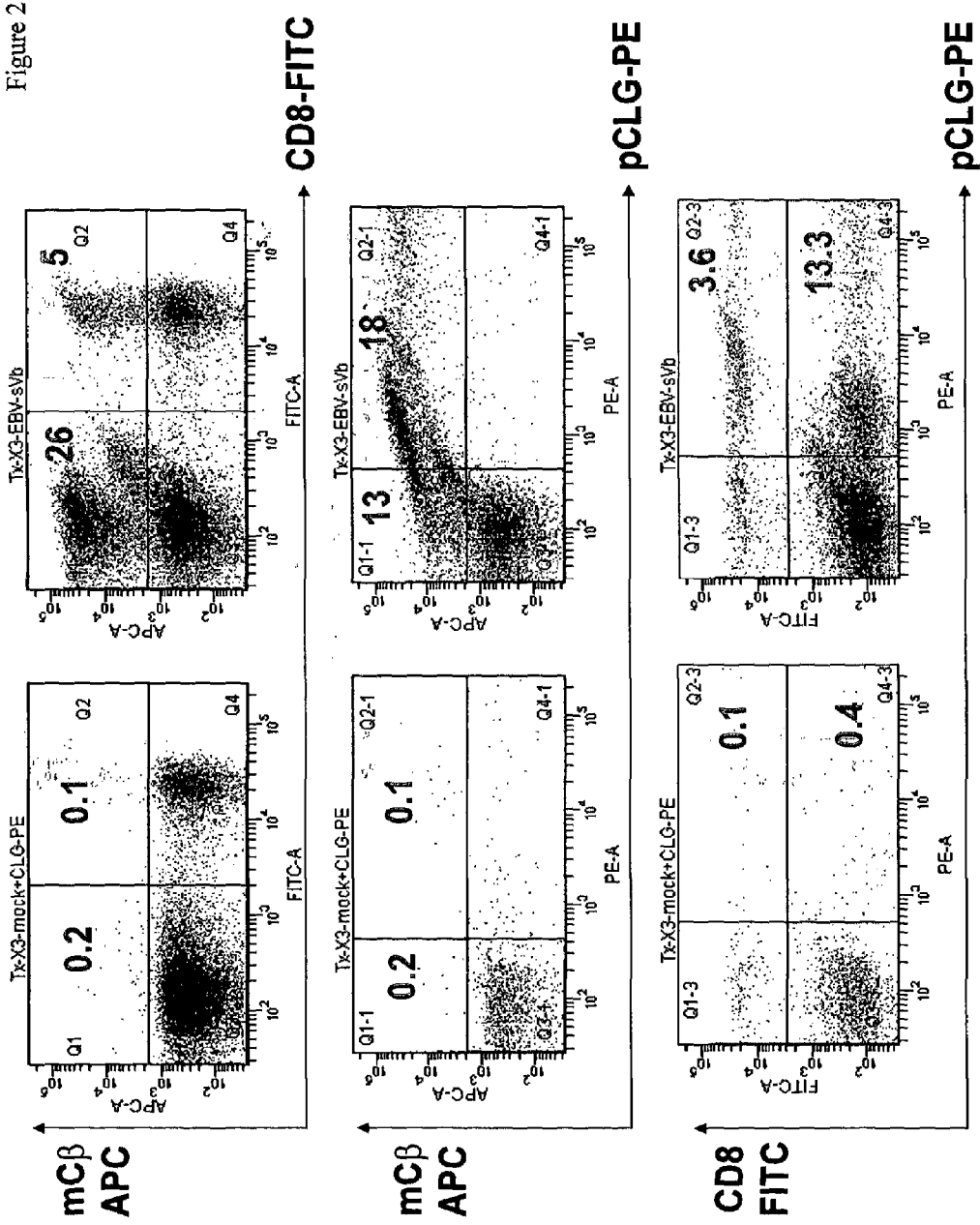
FIG. 2—EBV-sVβ-TCR transduction of huPBMC
FIG. 3—EBV-sVβ-TCR-X3-CD4-cytk
FIG. 4—EBV-sVβ-TCR-X3-CD8-cytk

Retroviral transfer of the LMP-2-specific TCR results in TCR expression on the surface of recipient T cells as determined by peptide/MHC tetramer staining and anti-Vβ13 antibody staining (FIG. 2).

Example 3

Intracellular Cytokine Staining of TCR Transduced T Cells

To demonstrate the functional antigen specific activity, the present inventors performed antigen specific stimulation and intracellular cytokine staining assays.

TCR-transduced T cells ($2 \times 10^5$) were incubated with $2 \times 10^5$ T2 stimulator cells coated with 100 mM relevant (pCLG: CLGGLLTMV) or irrelevant (pNLV: NLVPMVATV) peptide in 200 ml of culture medium containing brefeldin A (Sigma-Aldrich) at 1 mg/ml. After an incubation period of 18 h at 37° C. with 5% $CO_2$, the cells were first stained for surface CD8 or CD4 and then fixed, permeabilized, and stained for intracellular IFNg, IL2 and TNFa using the Fix & Perm kit (Caltag) according to the manufacturer's instructions. Samples were acquired on a LSR II flow cytometer and the data was analyzed using FACSDiva software (BD Biosciences).

Figure 3:
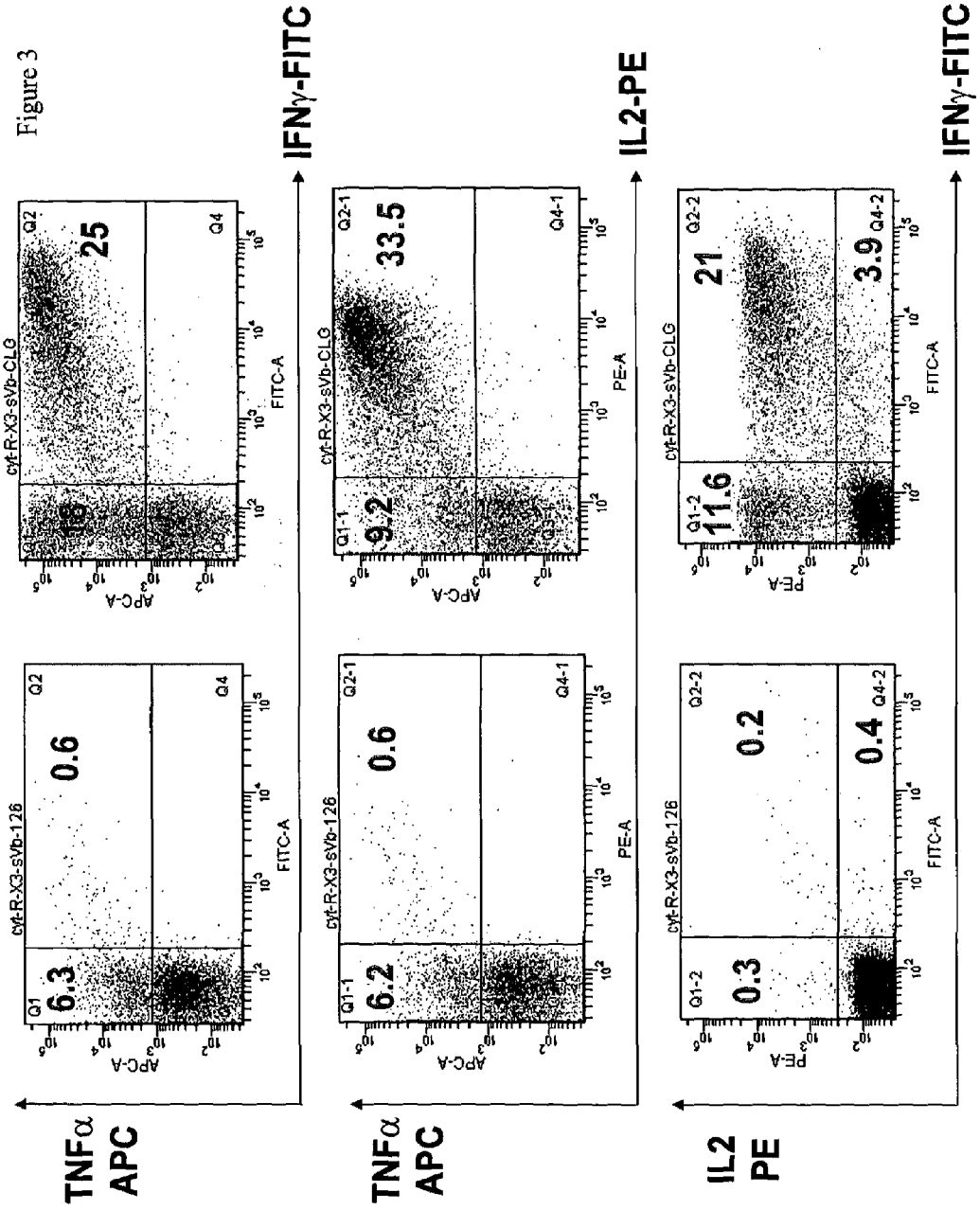
Figure 4:
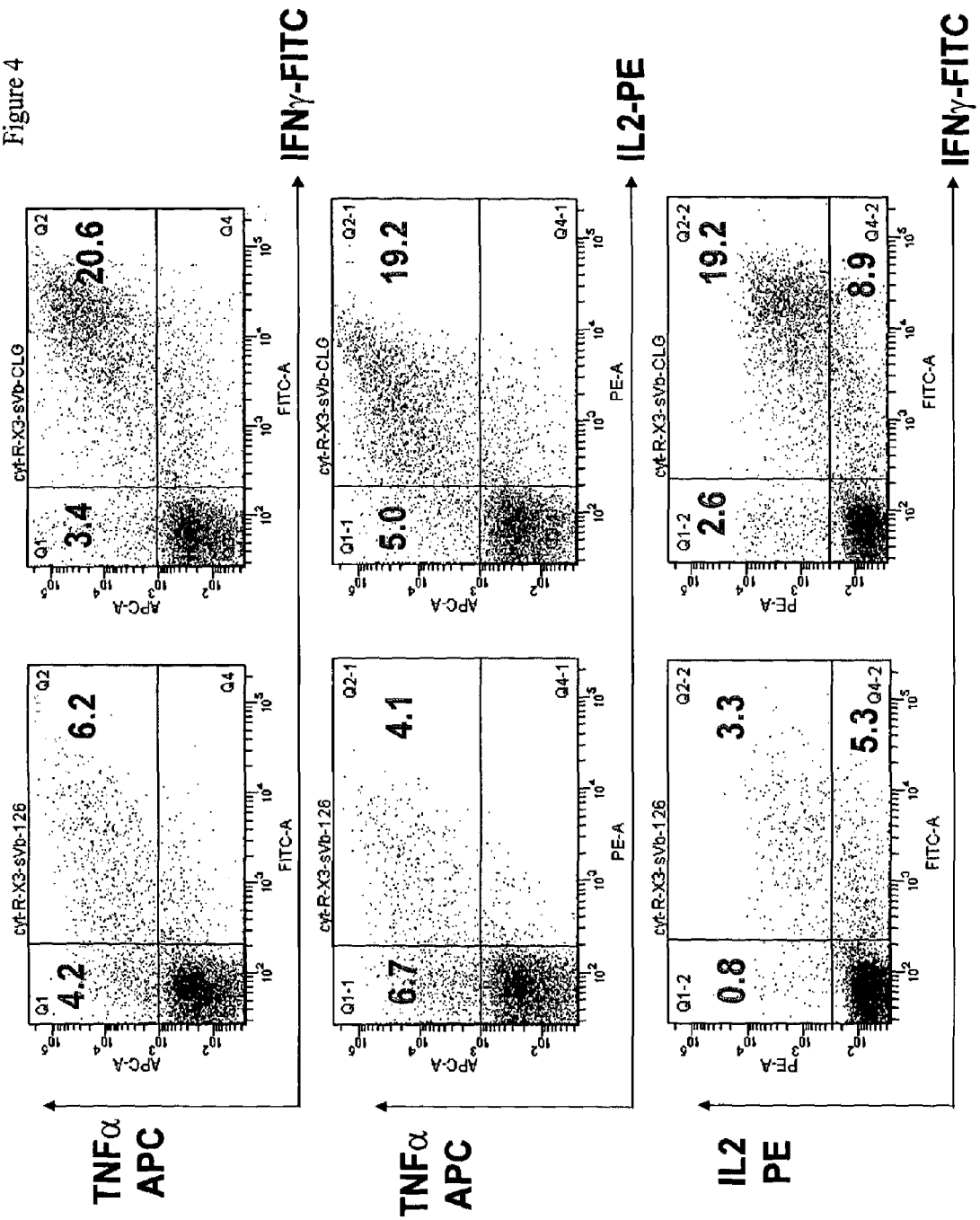

The results are shown in FIGS. 3 and 4.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An isolated T-cell receptor (TCR) which binds to a peptide from latent membrane protein 2 (LMP-2) from the Epstein Barr Virus (EBV), said peptide having the amino acid sequence CLGGLLTMV (SEQ ID No. 1) when presented by a major histocampatability complex (MHC) molecule, the TCR comprising an α chain and a β chain, wherein the α chain comprises three complementarity determining regions (CDRs) having the following amino acid sequences:

```
                                              (SEQ ID No. 4)
CDR1α-TSDQSYG (SEQ ID No. 5)
CDR2α-QGSYDEQ (SEQ ID No. 2)
CDR3α-FCAMREGSGSARQLTFGSGTQLTVLPD
``` and wherein the β chain comprises three complementarity determining regions (CDRs) having the following amino acid sequences:

```
                                              (SEQ ID No. 6)
CDR1β-SSHAT (SEQ ID No. 7)
CDR2β-FNYEAQ (SEQ ID No. 3)
CDR3β-ASSLGPAGIQETQYFGPGTRLLVL.
```

2. A TCR according to claim 1 which comprises the amino acid sequence shown as SEQ ID No. 8 or a variant thereof having at least 80% amino acid sequence identity.

3. A TCR according to claim 1 which comprises one or more mutations at the TCR α chain/β chain interface, such that when the TCR α chain and β chain are expressed in a T-cell, the frequency of mis-pairing between these chains and the endogenous TCR α chain and β chain is reduced.

4. A TCR according to claim 3, wherein the constant region domains of the α chain and β chain each comprise an additional cysteine residue, enabling the formation of an extra disulphide bond between the α chain and the β chain.

5. A method for treating or preventing a disease associated with Epstein Barr Virus (EBV) in a subject comprising the step of adoptive transfer of a EBV-specific T-cell to the subject, wherein the EBV-specific T-cell is made by transferring a gene to the subject, wherein the gene encodes the TCR of claim 1.

6. The method of claim 5, wherein the disease associated with EBV is EBV-positive Hodgkin's Lymphoma, EBV-positive Burkitt Lymphoma, EBV-positive nasopharyngeal carcinoma, or an EBV-positive post-transplant lymphoproliferative disorder (PTLD).

* * * * *

UNITED STATES PATENT AND TRADEMARK OFFICE
CERTIFICATE OF CORRECTION

PATENT NO. : 8,889,141 B2  
APPLICATION NO. : 13/498561  
DATED : November 18, 2014  
INVENTOR(S) : Hans Stauss et al.

Page 1 of 1

It is certified that error appears in the above-identified patent and that said Letters Patent is hereby corrected as shown below:

<u>In the Claims:</u>

Column 29, line 30, claim 1 "histocampatability" should be -- histocompatability --.

Column 30, line 28, claim 2 "A" should be -- The --.

Column 30, line 31, claim 3 "A" should be -- The --.

Column 30, line 36, claim 4 "A" should be -- The --.

Signed and Sealed this  
Twenty-third Day of February, 2016

Michelle K. Lee  
*Director of the United States Patent and Trademark Office*

```
                          SEQUENCE LISTING

<160> NUMBER OF SEQ ID NOS: 13

<210> SEQ ID NO 1
<211> LENGTH: 9
<212> TYPE: PRT
<213> ORGANISM: Epstein Barr Virus (EBV)

<400> SEQUENCE: 1

Cys Leu Gly Gly Leu Leu Thr Met Val
1               5

<210> SEQ ID NO 2
<211> LENGTH: 27
<212> TYPE: PRT
<213> ORGANISM: Homo sapiens

<400> SEQUENCE: 2

Phe Cys Ala Met Arg Glu Gly Ser Gly Ser Ala Arg Gln Leu Thr Phe
1               5                   10                  15

Gly Ser Gly Thr Gln Leu Thr Val Leu Pro Asp
            20                  25

<210> SEQ ID NO 3
<211> LENGTH: 24
<212> TYPE: PRT
<213> ORGANISM: Homo sapiens

<400> SEQUENCE: 3

Ala Ser Ser Leu Gly Pro Ala Gly Ile Gln Glu Thr Gln Tyr Phe Gly
1               5                   10                  15

Pro Gly Thr Arg Leu Leu Val Leu
            20

<210> SEQ ID NO 4
<211> LENGTH: 7
<212> TYPE: PRT
<213> ORGANISM: Homo sapiens

<400> SEQUENCE: 4

Thr Ser Asp Gln Ser Tyr Gly
1               5

<210> SEQ ID NO 5
<211> LENGTH: 7
<212> TYPE: PRT
<213> ORGANISM: Homo sapiens

<400> SEQUENCE: 5

Gln Gly Ser Tyr Asp Glu Gln
1               5
```

<210> SEQ ID NO 6
<211> LENGTH: 5
<212> TYPE: PRT
<213> ORGANISM: Homo sapiens

<400> SEQUENCE: 6

Ser Ser His Ala Thr
1               5

<210> SEQ ID NO 7
<211> LENGTH: 6
<212> TYPE: PRT
<213> ORGANISM: Homo sapiens

<400> SEQUENCE: 7

Phe Asn Tyr Glu Ala Gln
1               5

<210> SEQ ID NO 8
<211> LENGTH: 603
<212> TYPE: PRT
<213> ORGANISM: Homo sapiens

<400> SEQUENCE: 8

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Gln Ser Tyr Gly Leu Phe Trp Tyr Lys Gln Pro Ser Ser Gly Glu
        50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Gly Ser Gly Ser Ala Arg Gln Leu Thr Phe Gly Ser
        115                 120                 125

Gly Thr Gln Leu Thr Val Leu Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

```
Ser Gly Ser Gly Ala Thr Asn Phe Ser Leu Leu Lys Gln Ala Gly Asp
            275                 280                 285

Val Glu Glu Asn Pro Gly Pro Met Gly Thr Ser Leu Leu Cys Trp Val
290                 295                 300

Val Leu Gly Phe Leu Gly Thr Asp His Thr Gly Ala Gly Val Ser Gln
305                 310                 315                 320

Ser Pro Arg Tyr Lys Val Thr Lys Arg Gly Gln Asp Val Thr Leu Arg
                325                 330                 335

Cys Asp Pro Ile Ser Ser His Ala Thr Leu Tyr Trp Tyr Gln Gln Ala
                340                 345                 350

Leu Gly Gln Gly Pro Glu Phe Leu Thr Tyr Phe Asn Tyr Glu Ala Gln
            355                 360                 365

Pro Asp Lys Ser Gly Leu Pro Ser Asp Arg Phe Ser Ala Glu Arg Pro
370                 375                 380

Glu Gly Ser Ile Ser Thr Leu Thr Ile Gln Arg Thr Glu Gln Arg Asp
385                 390                 395                 400

Ser Ala Met Tyr Arg Cys Ala Ser Ser Leu Gly Pro Ala Gly Ile Gln
                405                 410                 415

Glu Thr Gln Tyr Phe Gly Pro Gly Thr Arg Leu Leu Val Leu Glu Asp
            420                 425                 430

Leu Arg Asn Val Thr Pro Pro Lys Val Ser Leu Phe Glu Pro Ser Lys
435                 440                 445

Ala Glu Ile Ala Asn Lys Gln Lys Ala Thr Leu Val Cys Leu Ala Arg
450                 455                 460

Gly Phe Phe Pro Asp His Val Glu Leu Ser Trp Trp Val Asn Gly Lys
465                 470                 475                 480

Glu Val His Ser Gly Val Cys Thr Asp Pro Gln Ala Tyr Lys Glu Ser
                485                 490                 495

Asn Tyr Ser Tyr Cys Leu Ser Ser Arg Leu Arg Val Ser Ala Thr Phe
            500                 505                 510

Trp His Asn Pro Arg Asn His Phe Arg Cys Gln Val Gln Phe His Gly
515                 520                 525

Leu Ser Glu Glu Asp Lys Trp Pro Glu Gly Ser Pro Lys Pro Val Thr
530                 535                 540

Gln Asn Ile Ser Ala Glu Ala Trp Gly Arg Ala Asp Cys Gly Ile Thr
545                 550                 555                 560

Ser Ala Ser Tyr His Gln Gly Val Leu Ser Ala Thr Ile Leu Tyr Glu
                565                 570                 575

Ile Leu Leu Gly Lys Ala Thr Leu Tyr Ala Val Leu Val Ser Gly Leu
            580                 585                 590

Val Leu Met Ala Met Val Lys Lys Lys Asn Ser
            595                 600

<210> SEQ ID NO 9
<211> LENGTH: 1812
<212> TYPE: DNA
<213> ORGANISM: Homo sapiens

<400> SEQUENCE: 9
atgtcacttt ctagcctgct gaaggtggtc acagcttcac tgtggctagg acctggcatt      60
gcccagaaga taactcaaac ccaaccagga atgttcgtgc aggaaaagga ggctgtgact     120
ctggactgca catatgacac cagtgatcaa agttatggtc tcttctggta caagcagccc     180
agcagtgggg aaatgatttt tcttatttat caggggtctt atgacgagca aaatgcaaca     240
```

```
gaaggtcgct actcattgaa tttccagaag gcaagaaaat ccgccaacct tgtcatctcc    300
gcttcacaac tgggggactc agcaatgtat ttctgtgcaa tgagagaggg ttctggttct    360
gcaaggcaac tgacctttgg atctgggaca caattgactg ttttacctga tatccagaac    420
cctgagcccg cggtgtacca gctgaaggac cccagaagcc aggacagcac cctgtgcctg    480
ttcaccgact cgacagcca gatcaacgtg cccaagacaa tggaaagcgg caccttcatc    540
accgacaagt gcgtgctgga catgaaggct atggacagca gagcaacgg cgccatcgcc    600
tggtccaacc agacctcctt cacatgccaa gacatcttca agagaccaa cgccacctac    660
cccagcagcg acgtgccctg cgatgccact ctcaccgaga gagcttcga gaccgacatg    720
aacctgaact tccagaacct gagcgtgatg ggcctgagaa tcctgctcct gaaagtggcc    780
ggcttcaacc tgctgatgac cctgcggctc tggagttctg gcagcggcgc taccaacttc    840
agcctgctga gcaggccgg cgacgtggag gaaaaccctg gccccatggg taccagtctc    900
ctatgctggg tggtcctggg tttcctaggg acagatcaca caggtgctgg agtctcccag    960
tctcccaggt acaaagtcac aaagagggga caggatgtaa ctctcaggtg tgatccaatt   1020
tcgagtcatg caacccttta ttggtatcaa caggccctgg ggcagggccc agagtttctg   1080
acttacttca attatgaagc tcaaccagac aaatcagggc tgcccagtga tcggttctct   1140
gcagagaggc ctgagggatc catctccact ctgacgattc agcgcacaga gcagcgggac   1200
tcagccatgt atcgctgtgc tagcagctta ggtcccgcag ggatccaaga acccagtac   1260
ttcgggccag gcacgcggct cctggtgctc gaggacctgc ggaacgtgac cccccccaag   1320
gtgtccctgt tcgagcccag caaggccgag atcgccaaca gcagaaagc cacactggtc   1380
tgtctggcta ggggcttctt ccccgaccac gtggagctgt cttggtgggt caacggcaaa   1440
gaagtccata cgcgcgtctg caccgaccct caggcttaca agagagcaa ctactcctac   1500
tgcctgagca gccggctgag agtgagcgcc accttctggc acaaccccg gaaccacttc   1560
cggtgccagg tgcagttcca cggcctgagc gaagaggaca gtggcctga gggctccccc   1620
aagcccgtga cccagaacat cagcgccgag gcctggggca gagccgactg cggcatcacc   1680
agcgccagct accaccaggg cgtgctgtcc gccaccatcc tgtacgagat cctgctgggc   1740
aaggccacac tgtacgccgt gctggtgtcc ggcctggtcc tgatggctat ggtgaagaag   1800
aagaacagct ga                                                       1812

<210> SEQ ID NO 10
<211> LENGTH: 497
<212> TYPE: PRT
<213> ORGANISM: Epstein Barr Virus (EBV)

<400> SEQUENCE: 10

Met Gly Ser Leu Glu Met Val Pro Met Gly Ala Gly Pro Pro Ser Pro
1               5                   10                  15

Gly Gly Asp Pro Asp Gly Asp Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95
```

-continued

```
Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
            115                 120                 125

Val Ala Pro Tyr Leu Phe Trp Leu Ala Ala Ile Ala Ala Ser Cys Phe
130                 135                 140

Thr Ala Ser Val Ser Thr Val Val Thr Ala Thr Gly Leu Ala Leu Ser
145                 150                 155                 160

Leu Leu Leu Leu Ala Val Ala Ser Ser Tyr Ala Ala Ala Gln Arg
            165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
            195                 200                 205

Leu Phe Ala Leu Leu Ala Ala Gly Gly Leu Gln Gly Ile Tyr Val
210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
            245                 250                 255

Leu Ile Val Asp Ala Val Leu Gln Leu Ser Pro Leu Gly Ala Val
            260                 265                 270

Thr Val Val Ser Met Thr Leu Leu Leu Ala Phe Val Leu Trp Leu
            275                 280                 285

Ser Ser Pro Gly Gly Leu Gly Thr Leu Gly Ala Ala Leu Leu Thr Leu
290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
            325                 330                 335

Leu Ile Cys Ser Ser Cys Ser Ser Cys Pro Leu Ser Lys Ile Leu Leu
            340                 345                 350

Ala Arg Leu Phe Leu Tyr Ala Leu Ala Leu Leu Leu Ala Ser Ala
            355                 360                 365

Leu Ile Ala Gly Gly Ser Ile Leu Gln Thr Asn Phe Lys Ser Leu Ser
            370                 375                 380

Ser Thr Glu Phe Ile Pro Asn Leu Phe Cys Met Leu Leu Leu Ile Val
385                 390                 395                 400

Ala Gly Ile Leu Phe Ile Leu Ala Ile Leu Thr Glu Trp Gly Ser Gly
            405                 410                 415

Asn Arg Thr Tyr Gly Pro Val Phe Met Cys Leu Gly Gly Leu Leu Thr
            420                 425                 430

Met Val Ala Gly Ala Val Trp Leu Thr Val Met Thr Asn Thr Leu Leu
            435                 440                 445

Ser Ala Trp Ile Leu Thr Ala Gly Phe Leu Ile Phe Leu Ile Gly Phe
450                 455                 460

Ala Leu Phe Gly Val Ile Arg Cys Cys Arg Tyr Cys Cys Tyr Tyr Cys
465                 470                 475                 480

Leu Thr Leu Glu Ser Glu Glu Arg Pro Pro Thr Pro Tyr Arg Asn Thr
            485                 490                 495

Val
```

<210> SEQ ID NO 11
<211> LENGTH: 378
<212> TYPE: PRT
<213> ORGANISM: Epstein Barr Virus (EBV)

<400> SEQUENCE: 11

Met Asn Pro Val Cys Leu Pro Val Ile Val Ala Pro Tyr Leu Phe Trp
1               5                   10                  15

Leu Ala Ala Ile Ala Ala Ser Cys Phe Thr Ala Ser Val Ser Thr Val
            20                  25                  30

Val Thr Ala Thr Gly Leu Ala Leu Ser Leu Leu Leu Leu Ala Ala Val
        35                  40                  45

Ala Ser Ser Tyr Ala Ala Gln Arg Lys Leu Leu Thr Pro Val Thr
    50                  55                  60

Val Leu Thr Ala Val Val Thr Phe Phe Ala Ile Cys Leu Thr Trp Arg
65                  70                  75                  80

Ile Glu Asp Pro Pro Phe Asn Ser Leu Leu Phe Ala Leu Leu Ala Ala
                85                  90                  95

Ala Gly Gly Leu Gln Gly Ile Tyr Val Leu Val Met Leu Val Leu Leu
            100                 105                 110

Ile Leu Ala Tyr Arg Arg Arg Trp Arg Arg Leu Thr Val Cys Gly Gly
        115                 120                 125

Ile Met Phe Leu Ala Cys Val Leu Val Leu Ile Val Asp Ala Val Leu
130                 135                 140

Gln Leu Ser Pro Leu Leu Gly Ala Val Thr Val Val Ser Met Thr Leu
145                 150                 155                 160

Leu Leu Leu Ala Phe Val Leu Trp Leu Ser Ser Pro Gly Gly Leu Gly
                165                 170                 175

Thr Leu Gly Ala Ala Leu Leu Thr Leu Ala Ala Ala Leu Ala Leu Leu
            180                 185                 190

Ala Ser Leu Ile Leu Gly Thr Leu Asn Leu Thr Thr Met Phe Leu Leu
        195                 200                 205

Met Leu Leu Trp Thr Leu Val Val Leu Leu Ile Cys Ser Ser Cys Ser
210                 215                 220

Ser Cys Pro Leu Ser Lys Ile Leu Leu Ala Arg Leu Phe Leu Tyr Ala
225                 230                 235                 240

Leu Ala Leu Leu Leu Leu Ala Ser Ala Leu Ile Ala Gly Gly Ser Ile
                245                 250                 255

Leu Gln Thr Asn Phe Lys Ser Leu Ser Ser Thr Glu Phe Ile Pro Asn
            260                 265                 270

Leu Phe Cys Met Leu Leu Leu Ile Val Ala Gly Ile Leu Phe Ile Leu
        275                 280                 285

Ala Ile Leu Thr Glu Trp Gly Ser Gly Asn Arg Thr Tyr Gly Pro Val
    290                 295                 300

Phe Met Cys Leu Gly Gly Leu Leu Thr Met Val Ala Gly Ala Val Trp
305                 310                 315                 320

Leu Thr Val Met Thr Asn Thr Leu Leu Ser Ala Trp Ile Leu Thr Ala
                325                 330                 335

Gly Phe Leu Ile Phe Leu Ile Gly Phe Ala Leu Phe Gly Val Ile Arg
            340                 345                 350

Cys Cys Arg Tyr Cys Cys Tyr Tyr Cys Leu Thr Leu Glu Ser Glu Glu
        355                 360                 365

Arg Pro Pro Thr Pro Tyr Arg Asn Thr Val
    370                 375

```
<210> SEQ ID NO 12
<211> LENGTH: 18
<212> TYPE: PRT
<213> ORGANISM: Epstein Barr Virus (EBV)

<400> SEQUENCE: 12

Gly Pro Val Phe Met Cys Leu Gly Gly Leu Thr Met Val Ala Gly Ala
1               5                   10                  15

Val Trp

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Asn Leu Val Pro Met Val Ala Thr Val
1               5
```